United States Patent [19]

Chen et al.

[11] 4,048,310

[45] Sept. 13, 1977

[54] TOPICAL STEROID FORMULATION IN FORM OF LOTION OR CREAM

[75] Inventors: James Ling Chen, East Brunswick; Jean M. Battaglia, North Brunswick, both of N.J.

[73] Assignee: E. R. Squibb & Sons, Inc., Princeton, N.J.

[21] Appl. No.: 660,963

[22] Filed: Feb. 24, 1976

[51] Int. Cl.$^2$ .................... A61K 31/56; A61K 31/58
[52] U.S. Cl. .................................. 424/238; 424/240; 424/241
[58] Field of Search ................... 424/238, 241, 240

[56] References Cited

U.S. PATENT DOCUMENTS

| | | | |
|---|---|---|---|
| 3,892,856 | 7/1975 | Hill et al. | 260/239.55 D |
| 3,892,857 | 7/1975 | Difazio et al. | 260/239.55 D |
| 3,900,561 | 8/1975 | Davis et al. | 424/238 |
| 3,971,772 | 7/1976 | Cemarusti et al. | 260/239.55 R |

*Primary Examiner*—Elbert L. Roberts
*Attorney, Agent, or Firm*—Lawrence S. Levinson; Merle J. Smith; Burton Rodney

[57] ABSTRACT

Steroid formulations in the form of creams or lotions which are used as topical anti-inflammatory agents are provided wherein the steroid, such as 21-chloro-9α-fluoro-Δ$^4$-pregnene-11β,16α,17α-triol-3,20-dione 16,17-acetonide, is at least partially dissolved in a ricinoleate vehicle such as castor oil.

25 Claims, No Drawings

TOPICAL STEROID FORMULATION IN FORM OF LOTION OR CREAM

The present invention relates to topical steroid formulations which include one or more ricinoleates, such as castor oil, as a vehicle for the steroid.

Topical steroid formulations containing 21-chloro9α-fluoro-Δ⁴-pregnene-11β, 16α, 17α-triol-3,20-dione 16,17 acetonide as the active ingredient are extensively employed in the treatment of skin disorders, such as dermatitis. To be therapeutically effective, the active ingredient must be in a molecular dispersion to facilitate desired percutaneous absorption which is particularly important in achieving a therapeutic response for the management of psoriasis. Unfortunately, the above steroid is insoluble in water (less than 0.0005% soluble) and is even less soluble in hydrocarbon vehicles such as mineral oil, petrolatum or polyethylene gelled mineral oil. Various organic solvents and solubilizers have been found to be good solvents for such steroid. However, they have been found to be unsuitable for commercial application for reasons such as their high volatility and low boiling points, their disagreeable odor, their "paint removing" property, and their undesirable skin reaction. Furthermore, various water-soluble emulsifiers and oil liquids or emollients have been suggested for use in preparing creams or lotions. However, because of the undesirably low solubility of the steroid in such vehicles, higher levels of these materials in topical products are requied thereby increasing their cost and also adversely affecting their cosmetic elegance.

Accordingly, in view of the above considerations, it is seen that a need exists for a suitable vehicle capable of solubilizing a sufficient amount of the steroid so that it may be employed in a topical formulation, while being dermatologically beneficial, stable, and pharmaceutically acceptable.

In accordance with the present invention, it has now been found that ricinoleates, such as castor oil, are excellent vehicles for 21-chloro-9α-fluoro-Δ⁴-pregnene-11β, 16α, 17α-triol-3,20-dione 16,17-acetonide as well as for other steroids such as 21-chloro-9-fluoro-2', 3'-dihydro-11β-hydroxy-5'-phenylpregna-1,4-dieno [16α, 17-b] [1,4]dioxin-3,20-dione dichloro methane solvate (1:1), and 9α-fluoro-11β, 16β, 17,21-tetrahydroxypregna-1,4-diene3,20-dione 16,17-acetonide (triamcinolone acetonide).

The topical steroid formulations of the invention comprises a steroid as described above, a ricinoleate vehicle, a preservative, water, an emulsifier-thickener, and an emollient or oleaginous material.

The ricinoleate vehicle may comprise one or more ricinoleates alone or in admixture with fatty acids or other vehicles and may be present in amounts within the range of from about 0.5 to about 20% by weight and preferably from about 1 to about 15% by weight of the steroid formulation depending upon the particular steroid employed. The preferred ricinoleate suitable for use herein is castor oil, that is ricinus oil or triglyceride of fatty acids, the fatty acid composition beng approximately 87% glyceryl ricinoleate, 7% oleic acid, 3% linoleate, 2% palmitate, 1% stearate and trace amounts of other compounds such as dihydroxystearic acid. Other examples of suitable ricinoleates include, but are not limited to, propylene glycol monoricinoleate, diglycol ricinoleate, and water-insoluble polyethylene glycol ricnioleates and the like.

The steroid will be present in an amount of form about 0.005 to about 0.6% by weight, and preferably from about 0.025 to about 0.2% based on the total weight of the composition, depending upon the type of steroid employed and its solubility in the ricinoleate vehicle. As will be seen hereinafter, other active ingredients may be employed in conjunction with the steroid. In such case, the other active ingredients, such as econazole, nystatin, neomycins, gramicidins and the like, or mixtures thereof, may be employed in amounts up to 2% or more.

The topical steroid formulations of the invention may take the form of a lotion or cream, that is, those formulations which include a relatively large aqueous phase and a relatively small oil phase. Furthermore, the lotions and creams of the invention may include the steroid component "all-in-solution" in the oil phase so that substantially no steroid crystallizes out at room temperature. Alternatively, the lotion or cream may comprise a biphasic system, that is, a system wherein a portion (from about 30 to about 75% by weight) of the steroid is in solution in the oil phase and the remainder of the steroid is in suspension in the aqueous phase.

With regard to the cream formulations of the invention where the steroid is to be all-in-solution, the cream will contain from about 0.005 to about 0.6% and preferably from about 0.025 to about 0.2% by weight of the active ingredient based on the weight of the entire cream formulation, and from about 0.5 to about 16% and preferably from about 1 to about 14% by weight of the ricinoleate based on the weight of the entire cream formulation and depending upon the solubility of the particular steroid in the particular ricinoleate employed. The all-in-solution cream formulation will also include in the oil phase, in addition to the steroid and ricinoleate, from about 5 to 14% and preferably from about 8 to about 12% by weight of the emulsifier-thickener based on the weight of the entire cream formulation, and from about 2 to about 8% and preferably from about 3 to about 5% by weight of oleaginous material or emollient based on the weight of the entire cream formulation. The oil phase may also optionally include an anti-whitening agent or anti-foaming agent in an amount within the range of from about 0.2 to about 3% and preferably from about 0.5 to about 1.5% by weight based on the entire cream formulation. An antioxidant may also optionally be included in an amount within the range of from about 0.005 to about 0.04% and preferably from abut 0.01 to about 0.03% by weight based on the entire cream formulation.

The aqueous phase of the all-in-solution cream formulation will contain a glycol-type preservative such as propylene glycol in an amount within the range of from about 10 to about 50% and preferably from about 12 to about 40% by weight of the entire cream formulation and/or a paraben or other conventional type preservative such as methyl and/or propyl paraben in an amount ranging from about 0.05 to about 0.5%, and purified water in an amount within the range of from about 30 to about 70% by weight and preferably from about 35 to about 65% by weight of the entire cream formulation.

With regard to the cream formulation of the invention in the form of the biphasic system, the cream will contain from about 0.6% and preferably from about 0.025 to about 0.2% by weight of the active ingredient based on the weight of the entire cream formulation, and from about 0.5 to about 14% and preferably from about 1 to about 8% by weight of the ricinoleate based on the weight of the entire cream formulation, depending upon the solubility of the particular steroid in the particular ricinoleate employed. The biphasic cream formulation will also include in the oil phase, in addition to the steroid and ricinoleate, from about 8 to about 12% and preferably from about 9 to about 11% by weight of the emulsifier-thickener based on the weight of the entire cream formulation, and from about 2 to about 8% and preferably from about 3 to about 6% by weight of oleaginous material or emollient based on the weight of the entire cream formulation. The oil phase may also optionally include an anti-whitening agent or anti-foaming agent in an amount within the range of from about 0.2 to about 3% and preferably from about 0.5 to about 1.5% by weight based on the entire cream formulation. An antioxidant may also optionally be included in an amount within the range of from about 0.05 to about 0.04% and preferably from about 0.01 to about 0.03% by weight based on the entire cream formulation.

The aqueous phase of the biphasic cream formulation will contain a preservative in amount within the range of from about 10 to about 50% and preferably from about 12 to about 40% by weight of the entire cream formulation, and purified water in an amount within the range of from about 30 to about 70% by weight and preferably from about 35 to about 65% by weight of the entire cream formulation.

With regard to the lotion formulation of the invention where the steroid is to be all-in-solution, the lotion will contain from about 0.005 to about 0.6% and preferably from about 0.025 to about 0.2% by weight of the active ingredient based on the weight of the entire lotion formulation, and from about 0.5 to about 16% and preferably from about 1 to about 14% by weight of the ricinoleate based on the weight of the entire lotion formulation, depending upon the solubility of the particular steroid in the particular ricinoleate employed. The all-in-solution lotion formulation will also include in the oil phase, in addition to the steroid and ricinoleate, from about 5 to about 14% and preferably from about 8 to about 121 % by weight of the emulsifier-thickener based on the weight of the entire lotion formulaion, and from about 0.5 to about 6% and preferably from about 1 to about 5% by weight of oleaginous material or emollient based on the weight of the entire lotion formulation. The oil phase may also optionally include an anti-whitening agent or anti-foaming agent in an amount within the range of from about 0.2 to about 3% and preferably from about 0.5 to about 1.5% by weight based on the entire lotion formualation. An antioxidant may also optionally be included in an amount within the range of from about 0.005 to about 0.04% and preferably from about 0.01 to about 0.03% by weight bsed on the entire lotion formulation.

The aqueous phase of the all-in-solution lotion formulation will contain glycol-type preservative in an amount within the range of from about 10 to about 50% an preferably from about 12 to about 40% by weight of the entire lotion formulaion, and/or a paraben or other conventional type preservative in amount ranging from about 0.05 to about 0.5%, and purified water in an amount within the range of about 50 to about 90% by weight an preferably from about 60 to about 85% by weight of the entire lotion formulation.

With regard to the biphasic lotion formuulation of the invention, the lotion wll contain from about 0.005 to about 0.6% and preferably from about 0.025 to about 0.2% by weight of the active ingredient based on the weight of the entire lotion formulation, and from about 0.5 to about 14% and preferably from 1 to about 8% by weight of the ricinoleate based on the weight of the entire lotion formulation, depending upon the solubility of the particular steroid in the particular ricinoleate employed. The biphasic lotion formulation will also include in the oil phase, in addition to the steroid and ricinoleate, from about 1 to about 5% and preferably from about 2 to about 4% by weight of the emulsifier-thickener based on the weight of the entire lotion formulation, and from about 0.2 to about 5% and preferably from about 0.5 to about 4% by weight of oleaginous material or emollient based on the weight of the entire lotion formulation. The oil phase may also optionally include an anti-whitening agent or anti-foaming agent in an amount within the range of from about 0.2 to about 3% and preferably from about 0.5 to about 1.5% by weight based on the entire lotion formulation. An antioxidant may also optionally be included in an amount within the range of from about 0.005 to about 0.04% and preferably from about 0.01 to about 0.03% by weight based on the entire lotion formulation.

The aqueous phase of the biphasic lotion formulation will contain a glycol-type preservative such as propylene glycol in an amount within the range of from about 8 to about 50% and preferably from about 10 to about 40% by weight of the entire lotion formulation, and/or paraben-type or other preservatives at their recommended amount as described above, and purified water in an amount within the range or from about 50 to about 90% by weight and preferably from about 60 to about 85% by weight of the entire lotion formulation.

With regard to specific steroid formulations, where 21-chloro-9α-fluoro-Δ⁴-pregnene-11β, 16α,17α-triol-3,20-dione 16,17-acetonide is employed in all-in-solution creams or lotions, the ricinoleate vehicle will be preferably employed in an amount within the range of from about 3 to about 16% by weight and more preferably within the range of from about 5 to about 12% by weight depending upon the amount of steroid employed; in the cse of biphasic formulations containing the above steroid, the ricinoleate vehicle will be preferably employed in an amount within the range of from about 3 to about 14% by weight and more preferably from about 5 to about 10% by weight depending upon the amount of steroid employed.

Where 21-chloro-9-fluoro-2′,3′-dihydro-11β-hydroxy-5′-phenylpregna-1,4-dieno[16α,17-b][1,4]dioxin-3,20-dione:dichloro methane solvate (1:1) acetonide is employed in all-in-solution creams or lotions, the ricinoleate vehicle will be preferably employed in an amount within the range of from about 0.5 to about 5% by weight and more preferably within the range of from about 1 to about 4% by weight depending upon the amount of steroid employed; in the case of biphasic formulation containing the above steroid, the ricinoleate vehicle will be preferably employed in an amount within the range of from about 0.5 to about 4% by weight and more preferably from about 1 to about 3% by weight depending upon the amount of steroid employed.

Where 9α-fluoro-11β,16α,17,21-tetrahydroxypregna-1,4-diene-3,20-dione 16,17-acetonide is employed in all-in-solution creams or lotions, the ricinoleate vehicle will be preferably employed in an amount within the range of from bout 3 to about 16% by weight and more preferably within the range of from about 5 to about 12% by weight depending upon the amount of steroid employed; in the case of biphasic formulations containing the above steroid, the ricinoleate vehicle will be preferably employed in an amount within the range of from about 3 to about 14% by weight and more preferably from about 5 to about 10% by weight depending upon the amount of steroid employed.

The emulsifier-thickener suitable for use herein may comprise ethers of polyethylene glycol and fatty alcohols, such as, Promulgen, Robinson Wagner Co., which contains some unreacted cetyl and stearyl alcohol, and other non-ionic emulsifying waxes such as Polawax, Croda Co.

The same emulsifier-thickener used in the cream formulation containing castor oil may also be obtained by substituting the above-mentioned emulsifying waxes with a mixture of polyoxyethylene (20) stearyl alcohol ether (BRIJ 78, ICI) or Polyoxyethylene (20) cetyl alcohol ether (BRIJ 58, ICI) with cetyl or stearyl alcohol. The ratio of the BRIJ or a mixture of the two BRIJ with the fatty alcohol or a mixture of the two alcohols should be within the range of from about 0.6 to about 3.5, preferably from about 1 to about 3.

Another emulsifier system suitable for use in the lotion or cream of the invention comprises a combination of glyceryl monostearate with polyoxyethylene sorbitan palmitate or stearate and cetyl or stearyl alcohol. For example, a cream or lotion containing 0.025% by weight 21-chloro-9α-fluoro-Δ$^4$-pregnene-11β,16α,17α-triol-3,20-dione 16,17-acetonide in solution in castor oil (4.5-6%), an oil-in-water cream, can be made with glyceryl monostearate (4.5-6%), cetyl or stearyl alcohol (9-11%) and Tween 60 (polyoxyethylene sorbitan monostearate 2.7-3.5%) is required. For 0.1% 21-chloro-9α-fluoro-Δ$^4$-pregnene-11β,16α,17α-triol-3,20-dione 16,17-acetonide cream higher levels of castor oil are required and Promulgen type emulsifier-thickeners are preferred. For topical steroids having higher solubility in castor oil, such as, 21-chloro-9-fluoro-2',3'-dihydro-11β-hydroxy-5'-phenylpregna-1,4-dieno[16α,17-b][1,4]dioxin-3,20-dione cichloro methane solvate (1:1) (approximately 42 mg/gm in castor oil), a 0.1% all-in-castor oil cream can be made with the second emulsion system containing glyceryl monostearate, cetyl alcohol and Tween 40 or 60.

It will also be appreciated that two or more materials may be employed to provide the emulsifying function and the thickening function. Thus, examples of emulsifying agents suitable for use herein include propylene glycol monostearate, as well as the non-ionic polyoxyalkylene derivatives of hexitol anhydride partial long chain fatty acid esters, e.g., the polyoxyalkylene derivatives of sorbitan monolaurate, sorbitan monopalmitate, sorbitan monostearate, sorbitan tristearate, sorbitan monooleate or sorbitan trioleate. These emulsifying agents are commercially available as Tween 20, 21, 40, 60, 65, 80, 81, and 85.

Thickeners suitable for use in combination with the above emulsifying agents include those conventionally employed in topical creams such as, for example, monoglycerides and fatty alcohols, fatty acid esters of alcohols having from about 3 to about 16 carbon atoms. Examples of suitable monoglycerides are glyceryl monostearate and glyceryl monopalmitate. Examples of fatty alcohols are cetyl alcohol and stearyl alcohol. Examples of suitable esters are myristyl stearate and cetyl stearate. The monoglyceride also functions as an auxilliary emulsifier. Other emollients or oleaginous material which may be employed include petrolatum, glyceryl monooleate, myristyl alcohol and isopropyl palmitate.

The anti-foaming anti-whitening agent increases the elegancy of the cream or lotion and inhibits the formation of a white soapy look upon rubbing the cream or lotion on the skin. An example of such a material suitable for use herein includes silicone fluid.

The cream or lotion may also contain an antioxidant such as butylated hydroxytoluene, butylated hydroxyanisole and the like for retarding rancidity of the castor oil or other ricinoleate and for protecting the steroid against oxidation.

The preservative suitable for use herein may comprise propylene glycol or parabens (para-hydroxy benzoates) with the propylene glycol being preferred because of less incidence of skip sensitivity.

The following examples illustrate preferred embodiments of the present invention without, however, limiting the same thereto. All temperatures are expressed in degrees Centigrade.

EXAMPLE 1

| Lotion, 0.025% (all-in-solution) | | |
|---|---|---|
| 21-chloro-9α-fluoro-Δ$^4$-pregnene-11β,16α,17α-triol-3,20-dione 16,17-acetonide, Micronized | 0.025 | gm. |
| Castor Oil, U.S.P. | 5.0 | gm. |
| Petrolatum, U.S.P. | 1.2 | gm. |
| Promulgen, Type D (PEG fatty alcohol ether) | 3.0 | gm. |
| Butylated Hydroxytoluene (BHT) | 0.020 | gm. |
| Propylene Glycol | 15.0 | gm. |
| Purified Water, sufficient to make | 100.0 | gm. |

The steroid and BHT are dissolved in castor oil with gentle heat not over 90° C. The petrolatum and Promulgen are melted together and heated to 75°-80° C and then mixed with the steroid-BHT solution. The resulting mixture is added to a hot 75°-80° C mixture of propylene glycol in 75 cc of purified water with vigorous agitation to emulsify. Agitation is continued until the temperature drops down to 48° C. Sufficient hot (48°-50° C) purified water is then added to make 100 gm. Mixing is then continued at a slow rate during the congealing stage until the temperature of the lotion reaches 42° C.

EXAMPLE 2

| Lotion, 0.025% (biphasic) | | |
|---|---|---|
| 21-chloro-9α-fluoro-Δ$^4$-pregnene-11β,16α,17α-triol-3,20-dione 16,17-acetonide, Micronized | 0.025 | gm. |
| Castor Oil, U.S.P. | 3.0 | gm. |
| Petrolatum, U.S.P. | 1.0 | gm. |
| Promulgen, Type D (PEG fatty alcohol ether) | 3.0 | gm. |
| Butylated Hydroxytoluene | 0.02 | gm. |
| Propylene Glycol | 15.0 | gm. |
| Purified Water, sufficient to make | 100.0 | gm. |

0.0125 gm of the steroid and BHT are dissolved in castor oil with gentle heat not over 90° C. Petrolatum and Promulgen D are melted together, heated to 75°-80° C and mixed with the steroid-BHT mixture. The resulting mixture is added to a hot 75°-80° C mixture of 10 gm propylene glycol in 75 cc of purified water with vigorous agitation to emulsify. Agitation is continued until the temperature drops down to 48° C and sufficient hot (48°-50° C) purified water is added to make 94 gm. Agitation is continued at a slow rate until the temperature reaches 45° C and a congealed cream forms. The remainder of the steroid is dispersed homogeneously in 5 gm of propylene glycol. 10 gm of the congealed cream is added to the steroid-glycol mix with thorough mixing until homogeneous. The remainder of the congealed cream is then added as well as sufficient water to make 100 gm and the mixture is mixed for about half an hour until a homogeneous lotion is formed.

EXAMPLE 3

| Topical Cream, 0.1% (all-in-solution) | | |
|---|---|---|
| 21-chloro-9α-fluoro-Δ⁴-pregnene-11β,16α,17α-triol-3,20-dione 16,17-acetonide, Micronized | 0.1 | gm. |
| Castor Oil, U.S.P. | 12.5 | gm. |
| Petrolatum, U.S.P. | 4.0 | gm. |
| Promulgen, Type D (PEG fatty alcohol ether) | 10.0 | gm. |
| Butylated Hydroxytoluene | 0.02 | gm. |
| Silicone Fluid DC 200, 350 cps. | 1.0 | gm. |
| Propylene Glycol Monostearate | 0.3 | gm. |
| Propylene Glycol | 15.0 | gm. |
| Purified Water, sufficient to make | 100.0 | gm. |

The steroid, propylene glycol monostearate and BHT are dissolved in castor oil with gentle heat, not over 90° C. Petrolatum and Promulgen D are melted together, and silicone fluid is added. After mixing, the mixture is added to the castor oil solution with thorough mixing, maintaining the temperature at 75°–80° C. Propylene glycol is mixed in 59 cc of water and heated to 80° C to form the aqueous phase which is added with vigorous agitation to the oil phase to emulsify. Agitation is continued until the temperature drops down to 48° C. Sufficient 50° C water is added to make 100 gm. Mixing is continued at a slow rate to congeal the mixture, until the temperature drops down to 42° C.

EXAMPLE 4

| Topical Cream, 0.1% (biphasic) | | |
|---|---|---|
| 21-chloro-9α-fluoro-Δ⁴-pregnene-11β,16α,17α-triol-3,20-dione 16,17-acetonide, Micronized | 0.1 | gm |
| Castor Oil, U.S.P. | 5.0 | gm. |
| Promulgen, Type D (PEG fatty alcohol ether) | 10.0 | gm. |
| Propylene Glycol Monostearate | 0.3 | gm. |
| Petrolatum, U.S.P. | 5.0 | gm. |
| Silicone Fluid DC 200, 350 cps. | 1.0 | gm. |
| Propylene Glycol | 15.0 | gm. |
| Butylated Hydroxytoluene | 0.02 | gm. |
| Purified Water, sufficient to make | 100.0 | gm. |

0.05 gm of the steroid is dissolved in castor oil with gentle heat not over 90° C. BHT and propylene glycol monostearate are added and the mixture is heated to dissolve all solids. Petrolatum and Promulgen D are melted, mixed together and heated to 75°–80° C. The two oil liquids and then mixed together with silicone oil and the temperature of the mixture is maintained.

10 gm. of propylene glycol and 60 cc of purified water are mixed together and heated to 75°–80° C. The aqueous solution is then poured into the oil phase with vigorous agitation to emulsify.

Agitation is continued until the temperature drops down to 48° C. Sufficient water is added to the emulsion to weigh 94.5 gm. Agitation is continued at a slow rate for congealing. Stirring is stopped when temperature reaches 42° C. 0.5 gm of steroid is homogeneously dispersed in 5 gm of propylene glycol and 20 gm of the cream is added and mixed thoroughly. The remainder of the cream is added and mixed until homogeneous (for about half an hour) to form the cream of the invention.

EXAMPLE 5

| Topical Cream | | |
|---|---|---|
| 21-chloro-9α-fluoro-Δ⁴-pregnene-11β,16α,17α-triol-3,20-dione 16,17-acetonide, Micronized (all-in-solution) | 0.025 | gm. |
| Econazole Nitrate | 1.0 | gm. |
| Castor Oil, U.S.P. | 3.0 | gm. |
| Petrolatum, U.S.P. | 8.0 | gm. |
| Promulgen, Type D | 14.0 | gm. |
| Silicone DC 200 Fluid | 1.0 | gm. |
| Propylene Glycol | 15.0 | gm. |
| Purified Water, sufficient to make | 100.0 | gm. |

The steroid is dissolved in castor oil with gentle heat not over 90° C. Petrolatum and Promulgen D are melted, mixed with silicone oil and heated to 80°–85° C and then mixed in the castor oil solution.

10 gm. of propylene glycol is dissolved in 57 cc. of purified water and heated to 80°–85° C. The hot aqueous solution is added to the oil phase with vigorous agitation to emulsify. The mixture is cooled to 55° C, and sufficient water is added to make 94 gm. The mixture is mixed at a slow rate until the temperature drops to 42° C. The econazole nitrate is homogeneously dispersed in 5 gm of propylene glyol and the resulting dispersion is incorporated geometrically into the above cream and mixed well.

EXAMPLE 6

| Topical Cream | | |
|---|---|---|
| 21-chloro-9α-fluoro-Δ⁴-pregnene-11β,16α,17α-triol-3,20-dione 16,17-acetonide, Micronized (all-in-solution) | 0.1 | gm. |
| Castor Oil, U.S.P. | 12.5 | gm. |
| Nystatin | 2.0 | gm. |
| Petrolatum, U.S.P. | 4.0 | gm. |
| Promulgen, Type D (PEG fatty alcohol ether) | 10.0 | gm. |
| Butylated Hydroxytoluene | 0.02 | gm. |
| Silicone Fluid DC 200, 350 cps. | 1.0 | gm. |
| Propylene Glycol | 15.0 | gm. |
| Purified Water, sufficient to make | 100.0 | gm. |

The steroid is dissolved in castor oil with gentle heat not over 90° C, and BHT is added with mixing to dissolve. Petrolatum and Promulgen D are melted and heated to 80°–85° C, silicone oil added thereto, and the mixture is incorporated into the castor oil portion. 10 gm. of propylene glycol is dissolved in 55 cc of water and heated to 80°–85° C and poured into the oil phase with vigorous agitation to emulsify. Mixing is continued until the temperature drops down to 48° C. Sufficient water is added to make 93 gm and mixing is continued at a slow rate until the temperature of the congealed cream drops down to 42° C. Nystatin is dispersed in 5 gm of propylene glycol and incorporated into the cream geometrically by thorough mixing for about 20–30 minutes.

EXAMPLE 7

| Lotion, 0.025% (all-in-solution) | | |
|---|---|---|
| 21-chloro-9-fluoro-2',3'-dihydro-11β-hydroxy-5'-phenylpregna-1,4-dieno[16α,17-b] [1,4]dioxin-3,20-dione:dichloro methane solvate (1:1) | 0.025 | gm. |
| Castor Oil, U.S.P. | 1.5 | gm. |
| Petrolatum, U.S.P. | 1.2 | gm. |
| Promulgen, Type D (PEG fatty alcohol ether) | 3.0 | gm. |

| Lotion, 0.025% (all-in-solution) | | |
|---|---|---|
| Butylated Hydroxytoluene (BHT) | 0.020 | gm. |
| Propylene Glycol | 15.0 | gm. |
| Purified Water, sufficient to make | 100.0 | gm. |

The steroid and BHT are dissolved in castor oil with gentle heat not over 90° C. The petrolatum and Promulgen are melted together and heated to 75°–80° C and then mixed with the steroid-BHT solution. The resulting mixture is added to a hot 75°–80° C mixture of propylene glycol in 75 cc of purified water with vigorous agitation to emulsify. Agitation is continued until the temperature drops down to 48° C. Sufficient hot (48°–50° C) purified water is then added to make 100 gm. Mixing is then continued at a slow rate until the temperature of the cream reaches 42° C.

EXAMPLE 8

| Lotion, 0.025% (biphasic) | | |
|---|---|---|
| 21-chloro-9-fluoro-2',3'-dihydro-11β-hydroxy-5'-phenylpregna-1,4-dieno[16α,17-b] [1,4]dioxin-3,20-dione:dichloro methane solvate (1:1) | 0.025 | gm. |
| Castor Oil, U.S.P. | 1.0 | gm. |
| Petrolatum, U.S.P. | 1.0 | gm. |
| Promulgen, Type D (PEG fatty alcohol ether) | 3.0 | gm. |
| Butylated Hydroxytoluene | 0.02 | gm. |
| Propylene Glycol | 15.0 | gm. |
| Purified Water, sufficient to make | 100.0 | gm. |

0.0125 gm of the steroid and BHT are dissolved in castor oil with gentle heat not over 90° C. Petrolatum and Promulgen D are melted together, heated to 75°–80° C and mixed with the steroid-BHT mixture. The resulting mixture is added to a hot 75°–80° C mixture of 10 gm propylene glycol in 75 cc of purified water with vigorous agitation to emulsify. Agitation is continued until the temperature drops down to 48° C and sufficient hot (48°–50° C) purified water is added to make 94 gm. Agitation is continued at a slow rate until the temperature reaches 45° C and a congealed cream forms. The remainder of the steroid is dispersed homogeneously in 5 gm of propylene glycol. 10 gm of the congealed cream is added to the steroid-glycol mix with thorough mixing until homogeneous. The remainder of the congealed cream is then added as well as sufficient water to make 100 gm and the mixture is mixed for about half an hour until a homogeneous lotion is formed.

EXAMPLE 9

| Topical Cream, 0.1% (all-in-solution) | | |
|---|---|---|
| 21-chloro-9-fluoro-2',3'-dihydro-11β-hydroxy-5'-phenylpregna-1,4-dieno[16α,17-b] [1,4]-dioxin-3,20-dione:dichloro methane solvate (1:1) | 0.1 | gm. |
| Castor Oil, U.S.P. | 4.0 | gm. |
| Petrolatum, U.S.P. | 4.0 | gm. |
| Promulgen, Type D (PEG fatty alcohol ether) | 10.0 | gm. |
| Butylated Hydroxytoluene | 0.02 | gm. |
| Silicone Fluid DC 200, 350 cps. | 1.0 | gm. |
| Propylene Glycol Monostearate | 0.3 | gm. |
| Propylene Glycol | 15.0 | gm. |
| Purified Water, sufficient to make | 100.0 | gm. |

The steroid, propylene glycol monostearate and BHT are dissolved in castor oil with gentle heat, not over 90° C. Petrolatum and Promulgen D are melted together, and silicone fluid is added. After mixing, the mixture is added to the castor oil solution with thorough mixing, maintaining the temperature at 75°–80° C. Propylene glycol is mixed in 59 cc of water and heated to 80° C to form the aqueous phase which is added with vigorous agitation to the oil phase to emulsify. Agitation is continued until the temperature drops down to 48° C. Sufficient 50° C water is added to make 100 gm. Mixing is continued at a slow rate to congeal the mixture, until the temperature drops down to 42° C.

EXAMPLE 10

| Topical Cream, 0.1% (biphasic) | | |
|---|---|---|
| 21-chloro-9-fluoro-2',3'-dihydro-11β-hydroxy-5'-phenylpregna-1,4-dieno[16,17-b] [1,4]dioxin-3,20-dione dichloro methane solvate (1:1) | 0.1 | gm. |
| Castor Oil, U.S.P. | 1.5 | gm. |
| Promulgen, Type D (PEG fatty alcohol ether) | 10.0 | gm. |
| Propylene Glycol Monostearate | 0.3 | gm. |
| Petrolatum, U.S.P. | 5.0 | gm. |
| Silicone Fluid DC 200, 350 cps. | 1.0 | gm. |
| Propylene Glycol | 15.0 | gm. |
| Butylated Hydroxytoluene | 0.02 | gm. |
| Purified Water, sufficient to make | 100.0 | gm. |

0.05 gm of the steroid is dissolved in castor oil with gentle heat not over 90° C. BHT and propylene glycol monostearate are added and the mixture is heated to dissolve all solids. Petrolatum and Promulgen D are melted, mixed together and heated to 75°–80° C. The two oil liquids are then mixed together with silicone oil and the temperature of the mixture is maintained.

10 gm. of propylene glycol and 60 cc of purified water are mixed together and heated to 75°–80° C. The aqueous solution is then poured into the oil phase with vigorous agitation to emulsify.

Agitation is continued until the temperature drops down to 48° C. Sufficient water is added to the emulsion to weigh 94.5 gm. Agitation is continued at a slow rate for congealing. Stirring is stopped when temperature reaches 42° C. 0.5 gm of steroid is homogeneously dispersed in 5 gm of propylene glycol and 20 gm of the cream is added and mixed thoroughly. The remainder of the cream is added and mixed until homogeneous (for about half an hour) to form the creams of the invention.

EXAMPLE 11

| Topical Cream | | |
|---|---|---|
| 21-chloro-9-fluoro-2',3'-dihydro-11β-hydroxy-5'-phenylpregna-1,4-dieno[16α,17-b] [1,4]dioxin-3,20-dione:dichloro methane solvate (1:1) (all-in-solution) | 0.025 | gm. |
| Econazole Nitrate | 1.0 | gm. |
| Castor Oil, U.S.P. | 1.0 | gm. |
| Petrolatum, U.S.P. | 8.0 | gm. |
| Promulgen, Type D | 14.0 | gm. |
| Silicone DC 200 Fluid | 1.0 | gm. |
| Propylene Glycol | 15.0 | gm. |
| Purified Water, sufficient to make | 100.0 | gm. |

The steroid is dissolved in castor oil with gentle heat not over 90° C. Petrolatum and Promulgen D are melted, mixed with silicone oil and heated to 80°–85° C and then mixed in the castor oil solution.

10 gm. of propylene glycol is dissolved in 57 cc. of purified water and heated to 80°–85° C. The hot aqueous solution is added to the oil phase with vigorous agitation to emulsify. The mixture is cooled to 55° C, and sufficient water is added to make 94 gm. The mixture is mixed at a slow rate until the temperature drops to 42° C. The econazole nitrate is homogeneously dispersed in 5 gm of propylene glycol and the resulting dispersion is incorporated geometrically into the above cream and mixed well.

EXAMPLE 12

| Topical Cream | | |
|---|---|---|
| 21-chloro-9-fluoro-2',3'-dihydro-11β-hydroxy-5'-phenylpregna-1,4-dieno[16α,17-b] [1,4]dioxin-3,20-dione:dichloro methane solvate (1:1) (all-in-solution) | 0.1 | gm. |
| Castor Oil, U.S.P. | 4.0 | gm. |
| Nystatin | 2.0 | gm. |
| Petrolatum, U.S.P. | 4.0 | gm. |
| Promulgen, Type D (PEG fatty alcohol ether) | 10.0 | gm. |
| Butylated Hydroxytoluene | 0.02 | gm. |
| Silicone Fluid DC 200, 350 cps. | 1.0 | gm. |
| Propylene Glycol | 15.0 | gm. |
| Purified Water, sufficient to make | 100.0 | gm. |

The steroid is dissolved in castor oil with gentle hat not over 90° C, and BHT is added with mixing to dissolve. Petrolatum and Promulgen D are melted and heated to 80°-85° C, silicone oil added thereto, and the mixture is incorporated into the castor oil portion. 10 gm. of propylene glycol is dissolved in 55 cc of water and heated to 80°-85° C and poured into the oil phase with vigorous agitation to emulsify. Mixing is continued until the temperature drops down to 48° C. Sufficient water is added to make 93 gm and mixing is continued at a slow rate until the temperature of the congealed cream down to 42° C. Nystatin is dispersed in 5 gm of propylene glycol and incorporated into the cream geometrically by thorough mixing for about 20-30 minutes.

EXAMPLE 13

| Lotion, 0.025% (all-in-solution) | | |
|---|---|---|
| 9α-fluoro-11β,16α,17,21-tetrahydroxypregna-1,4-diene-3,20-dione 16,17-acetonide | 0.025 | gm. |
| Castor Oil, U.S.P. | 5.0 | gm. |
| Petrolatum, U.S.P. | 1.2 | gm. |
| Promulgen, Type D (PEG fatty alcohol ether) | 3.0 | gm. |
| Butylated Hydroxytoluene (BHT) | 0.020 | gm. |
| Propylene Glycol | 15.0 | gm. |
| Purified Water, sufficient to make | 100.0 | gm. |

The steroid and BHT are dissolved in castor oil with gentle heat not over 90° C. The petrolatum and Promulgen are melted together and heated to 75°-80° C and then mixed with the steroid-BHT solution. The resulting mixture is added to a hot 75°-80° C mixture of propylene glycol in 75 cc of purified water with vigorous agitation to emulsify. Agitation is continued until the temperature drops down to 48° C. Sufficient hot (48°-50° C) purified water is then added to make 100 gm. Mixing is then continued at a slow rate until the temperature of the cream reaches 42° C.

EXAMPLE 14

| Lotion, 0.025% (biphasic) | | |
|---|---|---|
| 9α-fluoro-11β, 16α,17,21-tetrahydroxypregna-1,4-diene-3,20-dione 16,17-acetonide | 0.025 | gm. |
| Castor Oil, U.S.P. | 3.0 | gm. |
| Petrolatum, U.S.P. | 1.0 | gm. |
| Promulgen, Type D (PEG fatty alcohol ether) | 3.0 | gm. |
| Butylated Hydroxytoluene | 0.02 | gm. |
| Propylene Glycol | 15.0 | gm. |
| Purified Water, sufficient to make | 100.0 | gm. |

0.0125 gm of the steroid and BHT are dissolved in castor oil with gentle heat not over 90° C. Petrolatum and Promulgen D are melted together, heated to 75°-80° C and mixed with the steroid-BHT mixture. The resulting mixture is added to a hot 75°-80° C mixture of 10 gm propylene glycol in 75 cc of purified water with vigorous agitation to emulsify. Agitation is continued until the temperature drops down to 48° C and sufficient hot (48°-50° C) purified water is added to make 94 gm. Agitation is continued at a slow rate until the temperature reaches 45° C and a congealed cream forms. The remainder of the steroid is dispersed homogeneously in 5 gm of propylene glycol. 10 gm of the congealed cream is added to the steroid-glycol mix with thorough mixing until homogeneous. The remainder of the congealed cream is then added as well as sufficient water to make 100 gm and the mixture is mixed for about half an hour until a homogeneous lotion is formed.

EXAMPLE 15

| Topical Cream, 0.1% (all-in-solution) | | |
|---|---|---|
| 9α-fluoro-11β,16α,17,21-tetrahydroxypregna-1,4-diene-3,20-dione 16,17-acetonide | 0.1 | gm. |
| Castor Oil, U.S.P. | 12.5 | gm. |
| Petrolatum, U.S.P. | 4.0 | gm. |
| Promulgen, Type D (PEG fatty alcohol ether) | 10.0 | gm. |
| Butylated Hydroxytoluene | 0.02 | gm. |
| Silicone Fluid DC 200, 350 cps. | 1.0 | gm. |
| Propylene Glycol Monostearate | 0.3 | gm. |
| Propylene Glycol | 15.0 | gm. |
| Purified Water, sufficient to make | 100.0 | gm. |

The steroid, propylene glycol monostearate and BHT are dissolved in castor oil with gentle heat, not over 90° C. Petrolatum and Promulgen D are melted together, and silicone fluid is added. After mixing, the mixture is added to the castor oil solution with thorough mixing, maintaining the temperature at 75°-80° C. Propylene glycol is mixed in 59 cc of water and heated to 80° C to form the aqueous phase which is added with vigorous agitation to the oil phase to emulsify. Agitation is continued until the temperature drops down to 48° C. Sufficient 50° C water is added to make 100 gm. Mixing is continued at a slow rate to congeal the mixture, until the temperature drops down to 42° C.

EXAMPLE 16

| Topical Cream, 0.1% (biphasic) | | |
|---|---|---|
| 9α-fluoro-11β,16α,17,21-tetrahydroxypregna-1,4-diene-3,20-dione 16,17-acetonide | 0.1 | gm. |
| Castor Oil, U.S.P. | 5.0 | gm. |
| Promulgen, Type D (PEG fatty alcohol ether) | 10.0 | gm. |
| Propylene Glycol Monostearate | 0.3 | gm. |
| Petrolatum, U.S.P. | 5.0 | gm. |
| Silicone Fluid DC 200, 350 cps. | 1.0 | gm. |
| Propylene Glycol | 15.0 | gm. |
| Butylated Hydroxytoluene | 0.02 | gm. |
| Purified Water, sufficient to make | 100.0 | gm. |

0.05 gm of the steroid is dissolved in castor oil with gentle heat not over 90° C. BHT and propylene glycol monostearate are added and the mixture is heated to dissolve all solids. Petrolatum and Promulgen D are melted, mixed together and heated to 75°-80° C. The two oil liquids are then mixed together with silicone oil and the temperature of the mixture is maintained.

10 gm. of propylene glycol and 60 cc of purified water are mixed together and heated to 75°–80° C. The aqueous solution is then poured into the oil phase with vigorous agitation to emulsify.

Agitation is continued until the temperature drops down to 48° C. Sufficient water is added to the emulsion to weigh 94.5 gm. Agitation is continued at a slow rate for congealing. Stirring is stopped when temperature reaches 42° C. 0.05 gm of steroid is homogeneously dispersed in 5 gm of propylene glycol and 20 gm of the cream is added and mixed thoroughly. The remainder of the cream is added and mixed until homogeneous (for about half an hour) to form the cream of the invention.

EXAMPLE 17

| Topical Cream | |
|---|---|
| 9α-fluoro-11β,16α,17,21-tetrahydroxypregna-1,4-diene-3,20-dione 16,17-acetonide (all-in-solution) | 0.025 gm. |
| Econazole Nitrate | 1.0 gm. |
| Castor Oil, U.S.P. | 3.0 gm. |
| Petrolatum, U.S.P. | 8.0 gm. |
| Promulgen, Type D | 14.0 gm. |
| Silicone DC 200 Fluid | 1.0 gm. |
| Propylene Glycol | 15.0 gm. |
| Purified Water, sufficient to make | 100.0 gm. |

The steroid is dissolved in castor oil with gentle heat not over 90° C. Petrolatum and Promulgen D are melted, mixed with silicone oil and heated to 80°–85° C and then mixed in the castor oil solution.

10 gm of propylene glycol is dissolved in 57 cc. of purified water and heated to 80°–85° C. The hot aqueous solution is added to the oil phase with vigorous agitation to emulsify. The mixture is cooled to 55° C, and sufficient water is added to make 94 gm. The mixture is mixed at a slow rate until the temperature drops to 42° C. The econazole nitrate is homogeneously dispersed in 5 gm of propylene glycol and the resulting dispersion is incorporated geometrically into the above cream and mixed well.

EXAMPLE 18

| Topical Cream | |
|---|---|
| 9α-fluoro-11β,16α,17,21-tetrahydroxypregna-1,4-diene-3,20-dione 16,17-acetonide (all-in-solution) | 0.1 gm. |
| Castor Oil, U.S.P. | 12.5 gm. |
| Nystatin | 2.0 gm. |
| Petrolatum, U.S.P. | 4.0 gm. |
| Promulgen, Type D (PEG fatty alcohol ether) | 10.0 gm. |
| Butylated Hydroxytoluene | 0.02 gm. |
| Silicone Fluid DC 200, 350 cps. | 1.0 gm. |
| Propylene Glycol | 15.0 gm. |
| Purified Water, sufficient to make | 100.0 gm. |

The steroid is dissolved in castor oil with gentle heat not over 90° C, and BHT is added with mixing to dissolve. Petrolatum and Promulgen D are melted and heated to 80°–85° C, silicone oil added thereto, and the mixture is incorporated into the castor oil portion. 10 gm. of propylene glycol is dissolved in 55 cc of water and heated to 80°–85° C and poured into the oil phase with vigorous agitation to emulsify. Mixing is continued until the temperature drops down to 48° C. Sufficient water is added to make 93 gm and mixing is continued at a slow rate until the temperature of the congealed cream drops down to 42° C. Nystatin is dispersed in 5 gm of propylene glycol and incorporated into the cream geometrically by thorough mixing for about 20–30 minutes.

What is claimed is:

1. A composition for topical application in the form of a cream or lotion, comprising at least one steroid wherein said steroid is selected from the group consisting of 21-chloro-9α-fluoro-Δ⁴-pregnene-11β, 16α,17α-triol-3,20-dione 16,17-acetonide; 21-chloro-9-fluoro-2',3'-dihydro-11β-hydroxy-5'-propylpregna-1,4-dieno[-16α,17-b][1,4]-dioxin-3,20-dione:dichloro methane solvate (1:1); and 9α-fluoro-11β, 16α,17,21-tetrahydroxypregna-1,4-diene-3,20-dione 16,17-acetonide, a ricinoleate vehicle in which said steroid is at least partially soluble, an emulsifier-thickener comprising a polyethylene glycol ether of a fatty alcohol, an oleaginous material or emollient, a preservative and water.

2. The composition as defined in claim 1 wherein said ricinoleate vehicle is castor oil.

3. The composition as defined in claim 1 wherein said steroid is present in an amount within the range of from about 0.005 to about 0.6% by weight of the composition said ricinoleate vehicle is present in an amount within the range of from about 0.5 to about 2% by weight of the composition, said emulsifier-thickener is present in an amount within the range of from about 1 to about 14% by weight of the composition, said oleaginous material or emollient is present in an amount within the range of from about 0.2 to about 8% by weight of the composition, said preservative is present in an amount within the range of from about 8 to about 50% by weight of the composition, and said water is present in an amount within the range of from about 30 to about 90% by weight water.

4. The composition as defined in claim 3 further including one or more antioxidants.

5. A composition as defined in claim 1 in the form of a cream wherein said steroid is all-in-solution, and said steroid is present in an amount within the range of from about 0.005 to about 0.6% by weight of the composition, said ricinoleate is present in an amount within the range of from about 0.5 to about 16% by weight of the composition, said emulsifier-thickener is present in an amount within the range of from about 5 to about 14% by weight of the composition, said oleaginous material or emollient is present in an amount within the range of from about 2 to about 8% by weight of the composition, said preservative is present in an amount within the range of from about 10 to about 50% by weight of the composition, and said water is present in an amount within the range of from about 30 to about 70% by weight of the compostion.

6. The composition as defined in claim 4 wherein said ricinoleate vehicle is castor oil.

7. A composition as defined in claim 1 in the form of a cream of the biphasic type, wherein said steroid is present in an amount within the range of from about 0.005 to about 0.6% by weight of the composition, said ricinoleate is present in an amount within the range of from about 0.5 to about 14% by weight of the composition, said emulsifier-thickener is present in an amount within the range of from about 8 to about 12% by weight of the composition, said oleaginous material or emollient is present in an amount within the range of from about 2 to about 8% by weight of the composition, said preservative is present in an amount within the range of from about 10 to about 50% by weight of the composition, and said water is present in an amount within the range of from about 30 to about 70% by weight of the composition.

8. The composition as defined in claim 7 wherein said ricinoleate vehicle is castor oil.

9. A composition as defined in claim 1 in the form of a lotion wherein said steroid is all-in-solution, said steroid is present in an amount within the range of from about 0.005 to about 0.6 % by weight of the composition, said ricinoleate is present in an amount within the range of from about 0.5 to about 16% by weight of the composition, said emulsifier-thickener is present in an amount within the range of from about 5 to about 14% by weight of the composition, aid oleaginous material or emollient is present in an amount within the range of from about 0.5 to about 6% by weight of the composition, said preservative is present in an amount within the range of from about 1 to about 50% by weight of the composition, and said water is present in an amount within the range of from about 50 to about 90% by weight of the compostion.

10. The composition as defined in claim 9 wherein said ricinoleate vehicle is castor oil.

11. A composition as defined in claim 1 in the form of a lotion of the biphasic type, wherein said steroid is present in an amount within the range of from about 0.005 to about 0.6% by weight of the composition, said ricinoleate is present in an amount within the range of from about 0.5 to about 14% by weight of the composition, said emulsifier-thickener is present in an amount within the range of from about 1 to about 5% by weight of the composition, said oleaginous material or emollient is present in an amount within the range of from about 0.2 to about 5% by weight of the composition, said preservative is present in an amount within the range of from about 8 to about 50% by weight of the composition, and said water is present in an amount within the range of from about 50 to about 90% by weight of the composition.

12. The composition as defined in claim 11 wherein said ricinoleate vehicle is castor oil.

13. A composition as defined in claim 1 wherein said steroid comprises 21-chloro-9α-fluoro-$\Delta^4$-pregnene-11β, 16α, 17α-triol-3,20-dione 16.17-acetonide.

14. A composition as defined in claim 1 wherein said steroid comprises 9α-fluoro-11β,16α,17,21-tetrahydroxypregna-1,4-diene-3,20-dione 16.17-acetonide.

15. A composition as defined in claim 1 wherein aid oleaginous material is petrolatum, said emulsifier-thickener is polyethylene glycol fatty alcohol ether, and said preservative is propylene glycol.

16. A composition as defined in claim 1 further including econazole, nystatin, neomycin, gramicidin or mixtures thereof.

17. A composition as defined in claim 1 further including nystatin or econazole.

18. A composition as defined in claim 1 wherein said steroid comprises 21-chloro-9-fluoro-2',3'-dihydro-11β-hydroxy-5'-phenylpregna-1,4-dieno[16α,17-b][1,4]dioxin-3,20-dione:dichloro methane solvate (1:1).

19. A method of treating dermatitis, which comprises administering topically an effecttive amount of a composition as defined in claim 1.

20. A method of treating dermatitis, which comprises administering topically an effective amount of a composition as defined in claim 3.

21. A method of treating dermatitis, which comprises administering topically an effective amount of a composition as defined in claim 5.

22. A method of treating dermatitis, which comprises administering topically an effective amount of a composition as defined in claim 7.

23. A method of treating dermatitis, which comprises administering topically an effective amount of a composition as defined in claim 9.

24. A method of treating dermatitis, which comprises administering topically an effective amount of a composition as defined in claim 11.

25. The composition as defined in claim 1 further including propylene glycol monostearate.

* * * * *

UNITED STATES PATENT OFFICE
CERTIFICATE OF CORRECTION

Patent No. 4,048,310   Dated September 13, 1977

Inventor(s) James Ling Chen et al

It is certified that error appears in the above-identified patent and that said Letters Patent are hereby corrected as shown below:

Column 1, line 8, after "21-chloro" insert a hyphen.
Column 1, line 48, "16β" should read --16α--.
Column 2, line 67, before "0.6%" insert --0.005 to about--.
Column 3, line 20, "0.05" should read --0.005--.
Column 3, line 45, "121%" should read --12%--.
Column 3, line 57, "bsed" should read --based--.
Column 3, line 62, "an" should read --and--.
Column 3, line 64, before "amount" insert --an--.
Column 3, line 67, "an" should read --and--.
Column 4, line 34, "or" should read --of--.
Column 4, line 45, "cse" should read --case--.
Column 5, line 30, "plamitate" should read --palmitate--.
Column 6, line 20, "skip" should read --skin--.
Column 7, line 56, "and" should read --are--.
Column 10, line 15, "dione dichloro" should read --dione:dichloro--.
Column 10, line 43, "creams" should read --cream--.
Column 11, line 19, "hat" should read --heat--.
Column 11, line 30, after "cream" insert --drops--.
Column 13, line 9, "0.05" should read --0.5--.
Column 14, line 9, "propylpregna" should read --phenylpregna--.
Column 14, line 23, "2%" should read --20%--.
Column 14, line 53, "claim 4" should read --claim 5--.

UNITED STATES PATENT OFFICE
CERTIFICATE OF CORRECTION

Patent No. 4,048,310   Dated September 13, 1977

Inventor(s) James Ling Chen et al

It is certified that error appears in the above-identified patent and that said Letters Patent are hereby corrected as shown below:

Column 15, line 17, "1" should read --10--.
Column 16, line 3, "16.17" should read --16,17--.
Column 16, line 6, "16.17" should read --16,17--.

Signed and Sealed this

Tenth Day of January 1978

[SEAL]

Attest:

RUTH C. MASON
Attesting Officer

LUTRELLE F. PARKER
Acting Commissioner of Patents and Trademarks